United States Patent
Chen et al.

(10) Patent No.: US 7,270,002 B2
(45) Date of Patent: Sep. 18, 2007

(54) HUMIDITY SENSOR ELEMENT, DEVICE AND METHOD FOR MANUFACTURING THEREOF

(75) Inventors: Hui Wen Chen, Yilan County (TW); Ren Jang Wu, Hsinchu (TW); Yi Lu Sun, Hsinchu (TW); Pi Guey Su, Hsinchu (TW)

(73) Assignee: Industrial Technology Research Institute (TW)

( * ) Notice: Subject to any disclaimer, the term of this patent is extended or adjusted under 35 U.S.C. 154(b) by 110 days.

(21) Appl. No.: 10/859,240

(22) Filed: Jun. 3, 2004

(65) Prior Publication Data

US 2005/0081625 A1    Apr. 21, 2005

(30) Foreign Application Priority Data

Oct. 21, 2003   (TW) ............................... 92129125 A (51) Int. Cl.
*G01N 19/00* (2006.01)
(52) U.S. Cl. ................. 73/335.02; 73/24.04; 29/592.1; 29/595; 29/25.35
(58) Field of Classification Search ............. 73/335.02, 73/29.01, 29.02, 29.05; 29/592.1, 825, 829, 29/842, 595, 25.35
See application file for complete search history.

(56) References Cited

U.S. PATENT DOCUMENTS

| | | | | |
|---|---|---|---|---|
| 4,681,855 A | * | 7/1987 | Huang ......................... | 436/39 |
| 5,338,430 A | * | 8/1994 | Parsonage et al. .......... | 204/412 |
| 2004/0058226 A1 | * | 3/2004 | Lamarre et al. ............. | 429/44 |
| 2004/0095043 A1 | * | 5/2004 | Jitsukawa et al. .......... | 310/337 |

OTHER PUBLICATIONS

Alexander Star et al., Sensing with Nafion Coated Carbon Nanotube Field-Effedt Transistors, Aug. 15, 2003, Electroanalysis 2004, 16, No. 1-2, p. 108-112.*

* cited by examiner

*Primary Examiner*—Hezron Williams
*Assistant Examiner*—Ryan Christensen
(74) *Attorney, Agent, or Firm*—Bacon & Thomas, PLLC (57) ABSTRACT

A humidity sensor element, a humidity sensor device and a method for manufacturing thereof are provided. The humidity sensor element includes a substrate having a nanocomposite film as sensing material, wherein said nanocomposite film consists of carbon nanotube/perfluorinated polymer with acid functional groups in weight ratio of 0.01-20; and at least a pair of electrodes, which contact with the sensing material at one or both side(s). The nanocomposite film increases the sensitivity of humidity sensor element such that even an infinitesimal amount of moisture can be detected with minimum detection limit of 15.76 $ppm_v$.

6 Claims, 7 Drawing Sheets

HUMIDITY SENSOR ELEMENT, DEVICE AND METHOD FOR MANUFACTURING THEREOF

BACKGROUND OF THE INVENTION

1. Field of the Invention

The present invention discloses a humidity sensor element, device and a method for manufacturing thereof. The humidity sensor element comprises a substrate having a nanocomposite film as sensing material, wherein said nanocomposite film contains carbon nanotube/perfluorinated polymer with acid functional groups; and at least a pair of electrodes, which contact with the sensing material at one or both side(s). The nanocomposite film is highly sensitive in detecting infinitesimal amount of moisture.

2. Description of Related Art

A sensor detects a physical or chemical variation in the outside environment, such as temperature, pressure or humidity through its sensing element, and converts the variation through a transduction element into electrical signals that may be transmitted and measured. It works by changing the resistance, capacitance, or oscillation frequency in piezoelectric effect. In the application of humidity sensor, the sensor element typically contains a moisture sensitive film. Such film may be (1) moisture-lyable film containing a conductive material (e.g. carbon particles); (2) moisture-absorbing film containing electrolytes; or (3) polymer electrolyte film.

However the first type of films exhibits the disadvantages of having narrow humidity measuring range that its resistance change is remarkable in high humidity environments, but relatively unapparent in low humidity environments. Besides having the problem of narrow humidity measuring range, the second type of films is not suitable for long-term use at high humidity environments, because the electrolytes contained therein can be diluted and lost due to excessive moisture adsorption. The third type of films has the problem that the film may be damaged because of rising temperature, as such the humidity detection may be influenced.

The applications of humidity sensor are conventionally restricted by their non-linearity at high (>90% RH) and low (<30% RH) humidity environments. TW Patent No. 494235 disclosed a humidity sensing film, which was a mixture of polyethylene oxide and lithium perchlorate, having measuring range of 10-95% RH and linear accuracy of 30-90% RH. TW Patent No. 507073 disclosed a humidity sensing film, which comprised cross-linked product of conductive polymer having unsaturated alkyene groups and had measuring range less than 90% RH and good linear accuracy. U.S. Pat. No. 5,741,540 related to a pyrochlore-type crystalline tungsten trioxide film having measuring range of 15-95% RH and linear accuracy of 20-90% RH.

In published literature, Neshkova et al. used chemically modified coatings of nitrated polystyrene as the sensing material having measuring range of 10-98% RH and linear accuracy of 10-70% RH. Okada et al. employed Nafion (Ag) film with detection range of 1000-15000 $ppm_v$, but the linear accuracy of the sensor is not satisfactory.

Along with the rapid progress of technology, the importance of low humidity detection rises as demands increase. For instance, many high-tech processes, such as semiconductor process, OLED packaging, and gas filling are carried in the very low-pressure or vacuum environment. The presence of moisture, a kind of residual gas in the process, would cause distinct and adverse changes to the properties of metals and semiconductor films, for example, blocking the optical components or corroding the mechanical components. Therefore, engineers have increasing needs for low-humidity detection and analysis technologies. But few of the currently available humidity sensors can accurately detect low-level moisture as constrained by the property of the material used. Thus the current focus of efforts to improve humidity instruments is to develop materials that offer measuring accuracy at low humidity.

The term "nanocomposite" first appeared in 1982-1983 as proposed by Roy & Komarneni and their colleagues. It is used to describe nanoheterogeneous material prepared by sol-gel technique, in which at least the size of one phase constituent is in the range of nanometer. A composite carries the characteristics and properties of individual hybrid materials. The phase morphology and interfacial properties of the composite thus formed influence significantly on its overall performance. As the particle size of dispersed phase decreases, the mixture effect is better and the interfacial force is stronger. Polymer nanocomposites possess many characteristics not observed in conventional composite materials, and the nanometer grade particle size helps boost the polymer property.

Piezoelectric quartz crystal, a quartz crystal sandwiched between a pair of gold electrodes, is used as a signal transduction element of piezoelectric sensor. It can convert the detection signal measured by sensing molecules into electronic signals and amplify so that the detection signal can be transmitted. The action of gold electrodes is primarily to introduce an oscillating electric field perpendicular to the chip surface to produce mechanical oscillation inside the crystal due to inverse piezoelectric effect. If quartz crystal has constant thickness, such mechanical oscillation will be generated at constant resonance frequency, which can be measured by a proper electron oscillator circuit. For AT-cut quartz crystal, variation of the mass of its electrode surface ($\Delta m$) has a linear relationship with variation of the oscillation frequency of the crystal ($\Delta F$), that is, $\Delta F \propto \Delta m$ according to the Sauerbrey equation. Therefore if we intend to selectively measure a particular analyte, we only need to deposit a layer of highly-specific sensing film on the electrode surface of quartz crystal and then place this sensor chip in the testing environment that contains the analyte to let said analyte adhere on the sensing electrode by affinity, and measure the amount of analyte adhered based on the change of the crystal oscillation. Because of its sensitivity to mass change, piezoelectric quartz crystal has been applied extensively in the manufacturing of sensors, particularly in sensors with high sensitivity, such as trace-gas sensor, trace-humidity sensor and biosensor.

This invention attempts to employ polymer nanocomposite material as humidity sensing film, which can improve the inaccuracy linearity of traditional humidity sensors at low humidity level, and combine the mass sensitivity feature of piezoelectric quartz crystal to provide a humidity sensor with sensitive detection of low humidity.

SUMMARY OF THE INVENTION

The objective of the present invention is to provide a humidity sensor element, which comprises a substrate having a nanocomposite film as sensing material, wherein said nanocomposite film contains carbon nanotube and perfluorinated polymer with acid functional groups mixed in the ratio of 0.01-20 by weight; and at least a pair of electrodes, which contact with the sensing material at one or both side(s).

The aforesaid carbon nanotube is single-walled carbon nanotube.

The aforesaid acid functional group is sulphonic group or carboxyl group, whereas the aforesaid perfluorinated polymer with acid functional groups is perfluorinated sulphonic acid type ion exchange resin.

The mixing ratio of aforesaid carbon nanotube to perfluorinated polymer with acid functional groups is preferably 0.04 by weight.

The aforesaid electrodes are selected from gold, silver, platinum or nickel cadmium alloy, preferably gold.

The aforesaid substrate can be any inert material that does not react with the nanocomposite, comprising, but not limited to, silicon, ceramic or plastic material.

The aforesaid silicon material comprises, but not limited to, indium tin oxide glass, silicon wafer, AT-cut quartz crystal, ST-cut quartz crystal, T-cut quartz crystal, or XT-cut quartz crystal. The aforesaid ceramic material comprises, but not limited to, barium titanate piezoelectric ceramics, lead titanate ceramics, aluminum oxide ceramics or lead zirconate titanate ceramics. The aforesaid plastic material comprises, but not limited to, thermoplastic or thermosetting material, such as polypropylene and polyethylene.

The aforesaid substrate is preferably AT-cut quartz crystal.

The aforesaid humidity sensor element can be further arranged with testing chamber, electron oscillator circuit, and frequency calculator to form a humidity sensor device.

Another objective of the present invention is to provide a humidity sensor device, which comprises a humidity sensor element comprising a substrate having a nanocomposite film as sensing material and at least a pair of electrodes, wherein said nanocomposite film contains carbon nanotube and perfluorinated polymer with acid functional groups mixed in the ratio of 0.01-20 by weight, and said electrodes contact with the sensing material at one or both side(s); a testing chamber where said humidity sensor element is disposed therein; an electron oscillator circuit which provides oscillating electric field to the humidity sensor element to produce mechanical oscillation; and a frequency calculator to calculate the oscillation frequency change in said humidity sensor element.

The aforesaid carbon nanotube is single-walled carbon nanotube.

The aforesaid acid functional group is sulphonic group or carboxyl group, whereas the aforesaid perfluorinated polymer with acid functional groups is perfluorinated sulphonic acid type ion exchange resin.

The mixing ratio of aforesaid carbon nanotube to perfluorinated polymer with acid functional groups is preferably 0.04 by weight.

The aforesaid electrodes are selected from gold, silver, platinum or nickel cadmium alloy, preferably gold.

The aforesaid substrate comprises, but not limited to, AT-cut quartz crystal, ST-cut quartz crystal, T-cut quartz crystal, or XT-cut quartz crystal.

The aforesaid substrate is preferably AT-cut quartz crystal.

Yet another objective of the present invention is to provide a method for manufacturing humidity sensor element, comprising the steps of: providing a substrate; arranging at least a pair of electrodes on said substrate; mixing carbon nanotube and perfluorinated polymer solution with acid functional groups; coating the mixture of carbon nanotube and perfluorinated polymer solution with acid functional groups on said electrodes by means of spin-coating method; and drying said solution to form a humidity sensor element having a nanocomposite film.

The aforesaid carbon nanotube is single-walled carbon nanotube.

The aforesaid acid functional group is sulphonic group or carboxyl group, whereas the aforesaid perfluorinated polymer with acid functional groups is perfluorinated sulphonic acid type ion exchange resin.

The mixing ratio of aforesaid carbon nanotube to perfluorinated polymer with acid functional groups is 0.01-20 by weight, preferably 0.04 by weight.

The aforesaid electrodes are selected from gold, silver, platinum or nickel cadmium alloy, preferably gold.

The aforesaid substrate can be any inert material that does not react with the nanocomposite, comprising, but not limited to, silicon, ceramic or plastic material.

The aforesaid silicon material comprises, but not limited to, indium tin oxide glass, silicon wafer, AT-cut quartz crystal, ST-cut quartz crystal, T-cut quartz crystal, or XT-cut quartz crystal. The aforesaid ceramic material comprises, but not limited to, barium titanate piezoelectric ceramics, lead titanate ceramics, aluminum oxide ceramics or lead zirconate titanate ceramics. The aforesaid plastic material comprises, but not limited to, thermoplastic or thermosetting materials, such as polypropylene and polyethylene.

The aforesaid substrate is preferably AT-cut quartz crystal.

The humidity sensor element disclosed in the present invention is coated with a nanocomposite containing carbon nanotube and perfluorinated polymer having acid functional group as humidity sensing film, offers high linear accuracy even at low humidity, superior to that of prior technologies. Accordingly, the invention provides a humidity sensor element with higher accuracy and better measuring ability at low humidity.

DETAILED DESCRIPTION OF THE INVENTION

Figure 1:
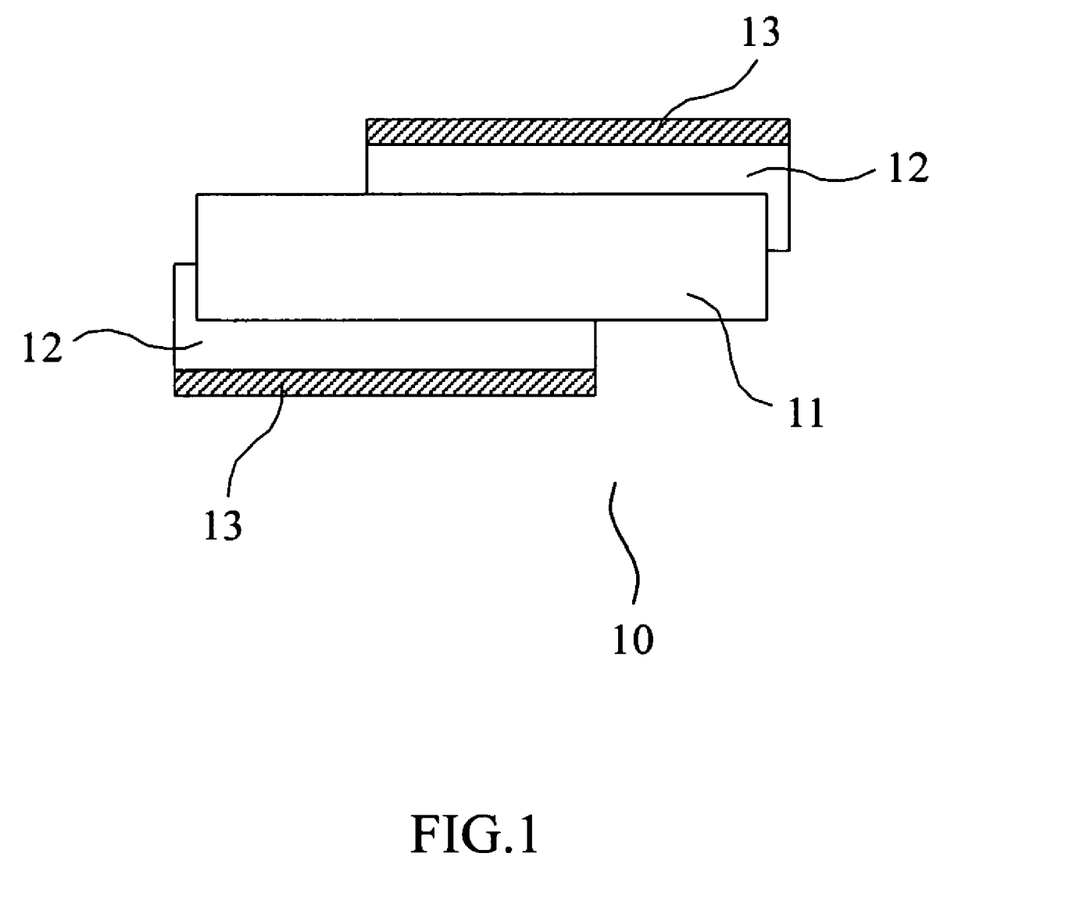
FIG. 1 shows the schematic diagram of humidity sensor element according to the present invention.

As shown in FIG. 1, the humidity sensor element 10 provided herein comprises a substrate 11 having a nanocomposite film 13 as sensing material, wherein said nanocomposite film contains carbon nanotube and perfluorinated polymer with acid functional groups; and at least a pair of electrodes 12 which contact with the nanocomposite film 13 at one or both side(s).

Said carbon nanotube is single-walled carbon nanotube; said acid functional group can be sulphonic group or carboxyl group; said perfluorinated polymer with acid functional group is perfluorinated sulphonic acid type ion exchange resin; the mixing ratio of carbon nanotube to perfluorinated polymer with acid functional groups is 0.01-20 by weight, preferably 0.04 by weight.

Said electrode 12 can be selected from gold, silver, platinum or nickel cadmium alloy, preferably gold.

Said substrate 11 can be any inert material that does not react with nanocomposite material, comprising, but not limited to, silicon, ceramic or plastic materials, wherein the silicon material comprises, but not limited to, indium tin oxide glass, silicon wafer, AT-cut quartz crystal, ST-cut quartz crystal, T-cut quartz crystal, or XT-cut quartz crystal; the ceramic material comprises, but not limited to, barium titanate piezoelectric ceramics, lead titanate ceramics, aluminum oxide ceramics or lead zirconate titanate ceramics; the plastic material comprises, but not limited to, thermoplastic or thermosetting materials, such as polypropylene or polyethylene.

Said substrate 11 is preferably AT-cut quartz crystal.

Said humidity sensor element 10 can be further arranged with testing chamber, electron oscillator circuit, and frequency calculator to form a humidity sensor device.

Figure 2:
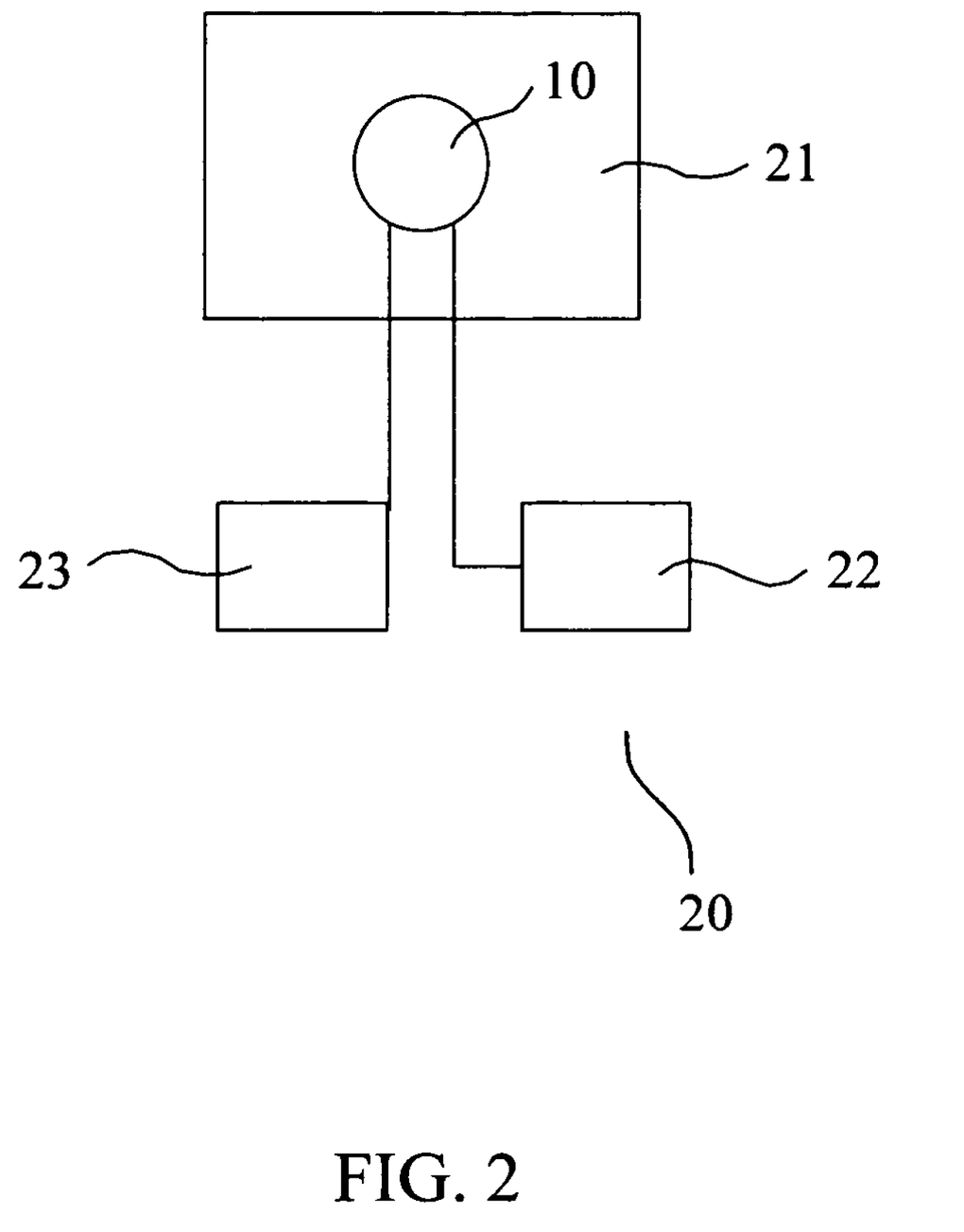
FIG. 2 shows the schematic diagram of humidity sensor device according to the present invention.

FIG. 2 shows the schematic diagram of humidity sensor device according to the present invention. The humidity sensor device 20 comprises a humidity sensor element 10 which can detect humidity variation; a testing chamber 21 where said humidity sensor element 10 is disposed therein; an electron oscillator circuit 22 which provides oscillating electric field to humidity sensor element 10 to produce mechanical oscillation; and a frequency calculator 23 to measure the oscillation frequency change of said humidity sensor element 10; wherein said humidity sensor element 10 comprises a substrate having a nanocomposite film containing carbon nanotube and perfluorinated polymer with acid functional groups as sensing material; and at least a pair of electrodes which contact with the sensing material at one or both side(s); wherein the mixing ratio of carbon nanotube to perfluorinated polymer with acid functional groups is 0.01-20 by weight, preferably 0.04 by weight.

Said humidity sensor device 20 measures humidity based on the piezoelectric frequency change, in which the piezoelectric substrate (e.g. quartz substrate) is sandwiched between a pair of metal electrodes (e.g. gold, silver, platinum or nickel cadmium alloy), and the electrodes introduce an oscillating electric field perpendicular to the surface of piezoelectric substrate. Said oscillating electric field forces the crystal lattice of the piezoelectric substrate to produce mechanical oscillation similar to standing waves, through which a constant frequency is generated. The key factor affecting the frequency of crystal oscillation is the changes of electrode mass. Thus the mass of substance (e.g. water molecules) adhered on the electrode may be computed by measuring the change of crystal's oscillation frequency. The present invention employs the theory described above to measure the humidity in the environment by monitoring the changes of oscillation frequency caused by the amount of water molecules adhered on the electrode, and furthermore, modifies said electrode surface with a newly developed nanocomposite film to give the humidity sensor element higher sensitivity to detect infinitesimal amount of moisture, and then to achieve lower humidity detection limit.

Figure 3:
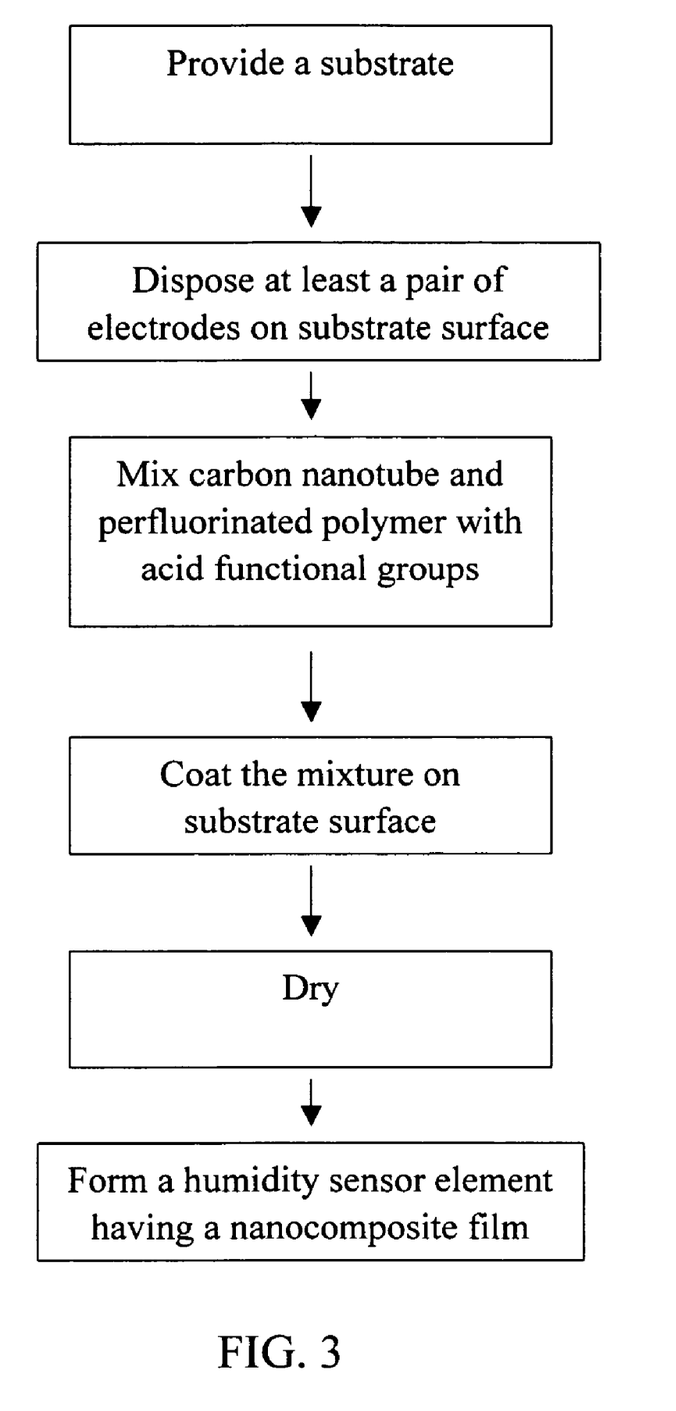
FIG. 3 shows the flow chart for manufacturing humidity sensor element according to the present invention.

FIG. 3 depicts the flow process for manufacturing a humidity sensor element according to this invention, comprising the steps of providing a substrate, which can be silicon material (e.g. AT-cut quartz crystal), ceramic material (e.g. aluminum oxide ceramics), or plastic material (e.g. polypropylene); disposing at least a pair of electrodes made of gold, silver, platinum or nickel cadmium alloy on said substrate, and preferably AT-cut quartz crystal having gold electrodes is used; next mixing uniformly carbon nanotube and perfluorinated polymer solution with acid functional groups in the ratio of 0.01-20 by weight, preferably 0.04 by weight; and coating said mixture solution by means of spin-coating method on said electrodes at preferably a speed of 1000 rpm for 3 minutes; and finally forming a humidity sensor element having a nanocomposite film.

The present invention and its efficacy are further depicted with the illustration of examples, but the descriptions made in the examples should not be construed as a limitation on the actual application of the present invention. All modifications and alterations made by those familiar with the skill without departing from the spirits of the invention and appended claims shall remain within the protected scope and claims of the invention.

EXAMPLES (A) Manufacturing of Humidity Sensor Element

Take 0.001 g of single-walled carbon nanotube (CNT, supplied by Carbon Technology, Inc., CAS Number: 7782-42-5) and 5 g of 0.5 wt. % Nafion (dissolved in the mixture of lower fatty alcohol and water, purchased from Aldrich, USA, which is perfluorinated ionic polymer containing small amount of sulphonic group or carboxyl group), and mix them thoroughly to form CNT/Nafion mixture. Drip the mixture on the gold electrodes of quartz crystal (AT-cut quartz crystal), spin coat at the speed of 1000 rpm for 3 minutes, and dry to obtain a humidity sensor element coated with CNT/Nafion nanocomposite film.

(B) Experimental Apparatus

Figure 4:
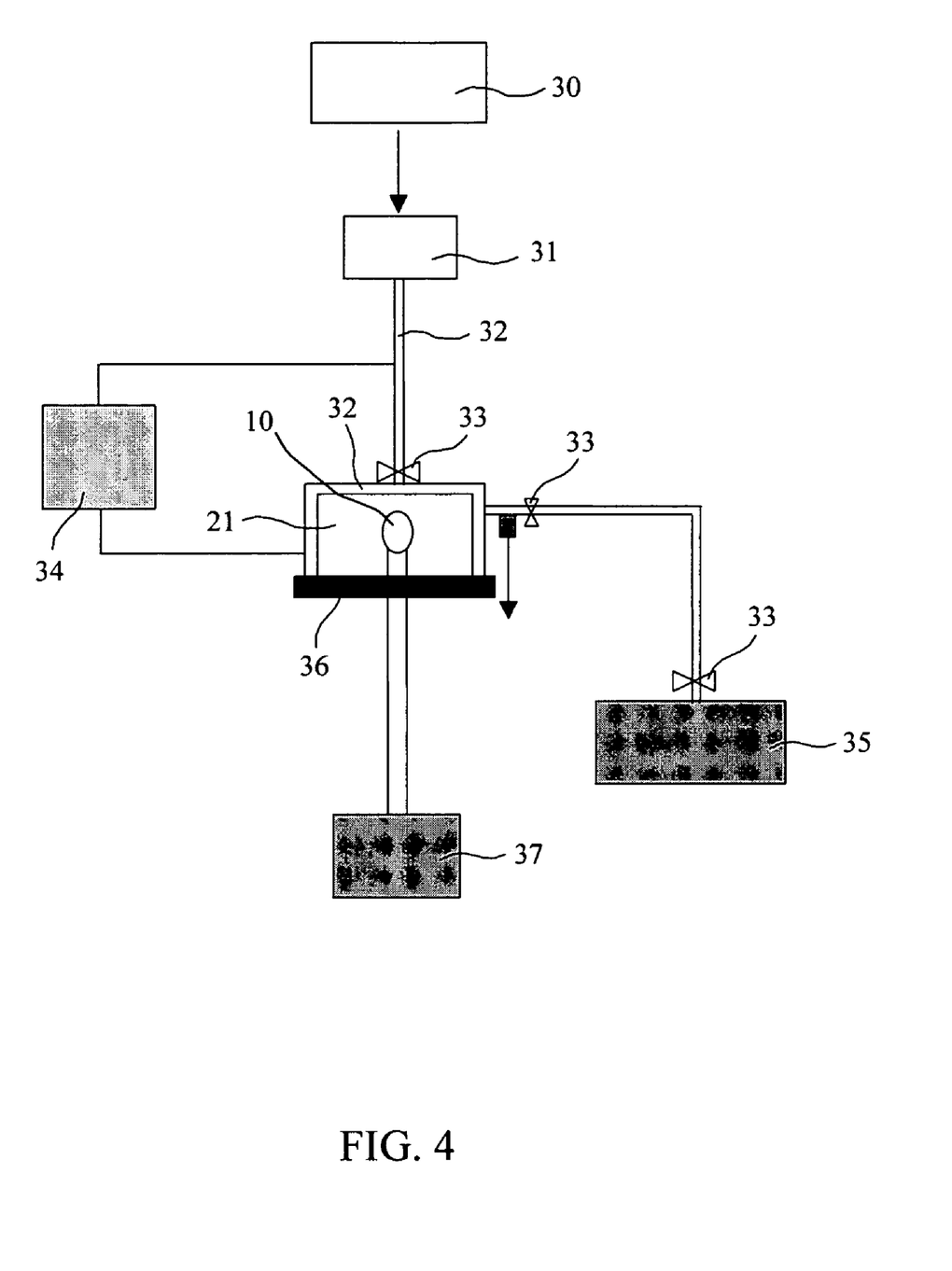
FIG. 4 shows the schematic diagram of experimental apparatus in an example of the present invention.

As shown in FIG. 4 which illustrates an apparatus for measuring low humidity in this example, the flow of gas produced by standard humidity generator 30 is controlled by flow controller 31, and the gas is heated by piping wrapped with heating tape 32 and enters into the testing chamber 21 after passing through two directional controlled valves 33. The temperature in the testing chamber 21 is controlled by heating tape 32 and temperature controller 34, and its pressure is maintained constant by vacuum pump 35. The testing chamber 21 contains the humidity sensor element 10, which can detect the humidity in the testing chamber 21 and connects with transduction device 37 consisting of electron oscillation circuit and frequency calculator through perforated guide 36. The transduction device 37 reveals the sensitivity of humidity sensor element 10 to humidity. The gas from the standard humidity generator 30 is also measured by optical chilled mirror dew point hygrometer (not shown in the diagram) for reference standard.

(C) Comparing the Performance of Humidity Sensor Element Coated with CNT/Nafion and Nafion Only Put humidity sensor element coated with CNT/Nafion nanocomposite film in the aforesaid testing chamber and let the water vapor concentration in the testing chamber change with time to test the performance of this sensor and compare it with sensor coated with Nafion only.

Figure 5:
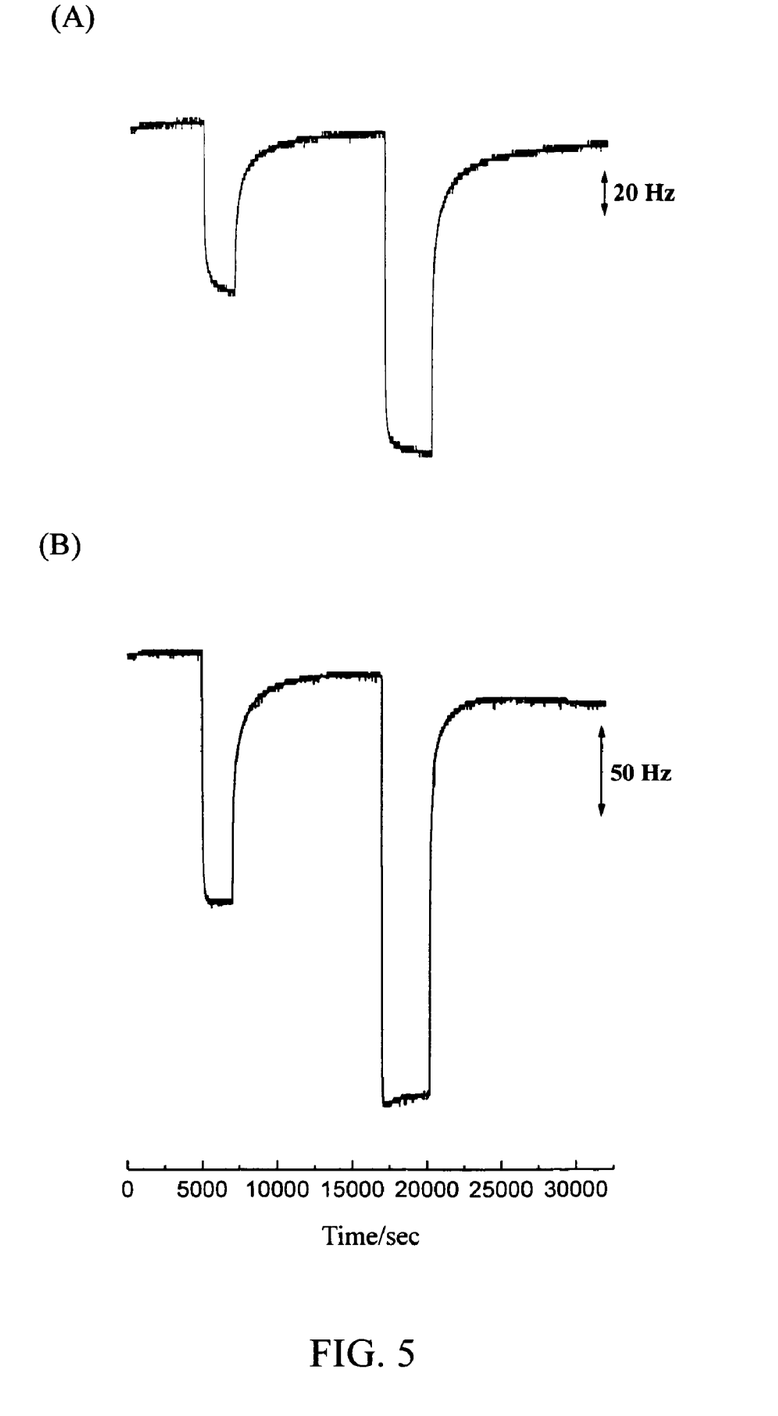
FIG. 5 shows effect of adding CNT on the sensitivity of humidity sensing for different water vapor content on (A) Nafion and (B) CNT/Nafion humidity sensor element.

FIG. 5 shows the frequency shift of sensor element under different water vapor concentration; FIG. 5(A) is that of sensor element coated with Nafion and FIG. 5(B) is that of sensor element coated with CNT/Nafion. The results show that under the same humidity condition, humidity sensor element added with CNT had rather high sensitivity, exhibiting greater frequency change than that of sensor element without CNT after trace moisture was introduced.

Table 1 depicts the frequency shifts and sensitivity of humidity sensor element under different water vapor content, where sensitivity is defined as $-\Delta Hz/\Delta ppm_v$. As shown, CNT/Nafion humidity sensor element had greater sensitivity than Nafion humidity sensor, particularly at low humidity. When moisture content was 15.76 $ppm_v$, frequency shifts of Nafion humidity sensor element were 8985325 Hz and its sensitivity was 1.61; frequency shifts of CNT/Nafion humidity sensor element were 8966159 Hz and its sensitivity was 4.86.

TABLE 1

| Moisture Content | Frequency Shifts (Hz) | | Sensitivity ($-\Delta Hz/\Delta ppm_v$) | |
|---|---|---|---|---|
| ($ppm_v$) | Nafion | CNT/Nafion | Nafion | CNT/Nafion |
| 15.76 | 8985325 | 8966159 | 1.61 | 4.86 |
| 311.61 | 8985262 | 8965962 | 0.25 | 0.77 |
| 825.95 | 8985198 | 8965839 | 0.17 | 0.43 |
| 1775.37 | 8985123 | 8965688 | 0.12 | 0.29 |
| 2714.40 | 8985061 | 8965572 | 0.10 | 0.23 |
| 3789.66 | 8984990 | 8965453 | 0.09 | 0.20 |
| 4586.66 | 8984924 | 8965349 | 0.09 | 0.18 |
| 6477.65 | 8984811 | 8965183 | 0.08 | 0.16 |
| 11104.14 | 8984425 | 8964709 | 0.08 | 0.13 |
| 15315.73 | 8983842 | 8964154 | 0.10 | 0.13 |

Figure 6:
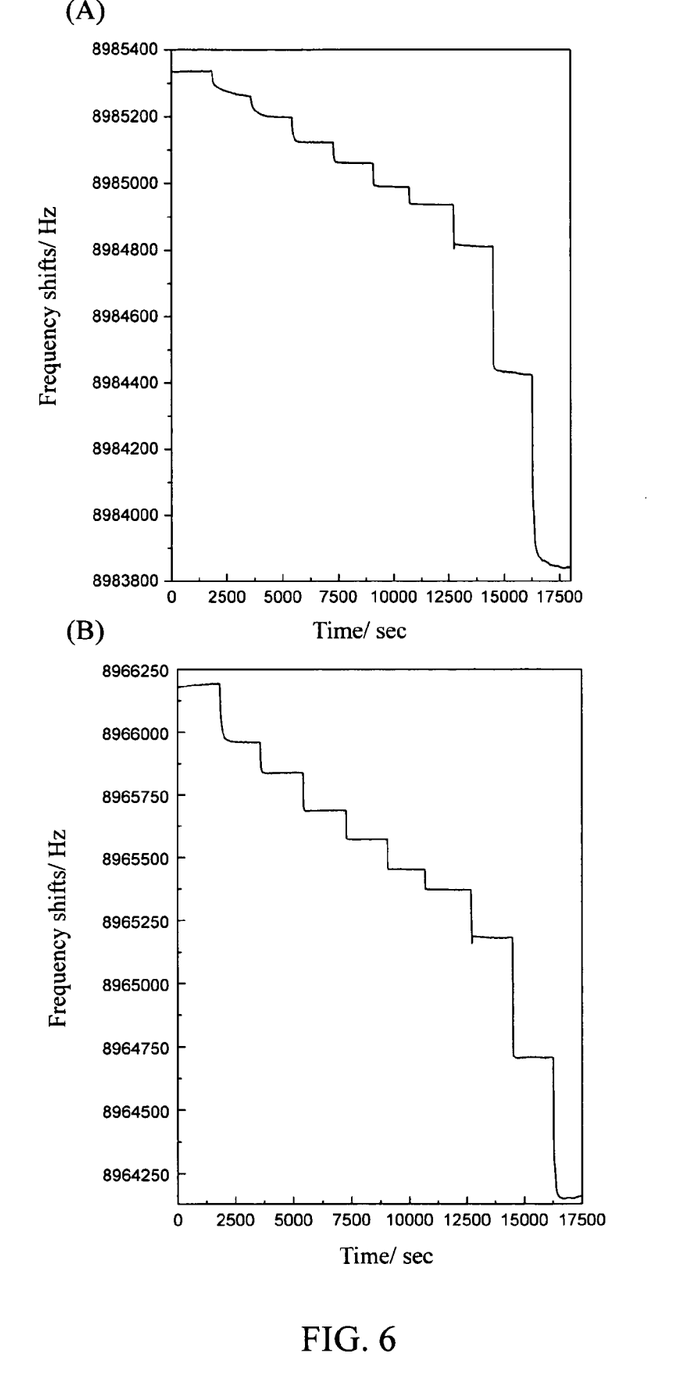
FIG. 6 shows frequency shifts as a function of time for different moisture content on (A) Nafion and (B) CNT/Nafion humidity sensor element.

FIG. 6 shows the relationships between time and frequency shifts measured by Nafion humidity sensor element and CNT/Nafion humidity sensor element under water vapor concentration of 8.46-15315.73 $ppm_v$, where FIG. 6(A) is the graph of frequency shifts versus time measured by Nafion coated humidity sensor and FIG. 6(B) is the graph of frequency shifts versus time measured by CNT/Nafion coated humidity sensor. As shown, at low humidity levels, the response time ($T_{90}$) of CNT/Nafion humidity sensor was less than 5 seconds, shorter than that of humidity sensor without CNT, and the thermodynamic equilibrium was achieved faster.

Figure 7:
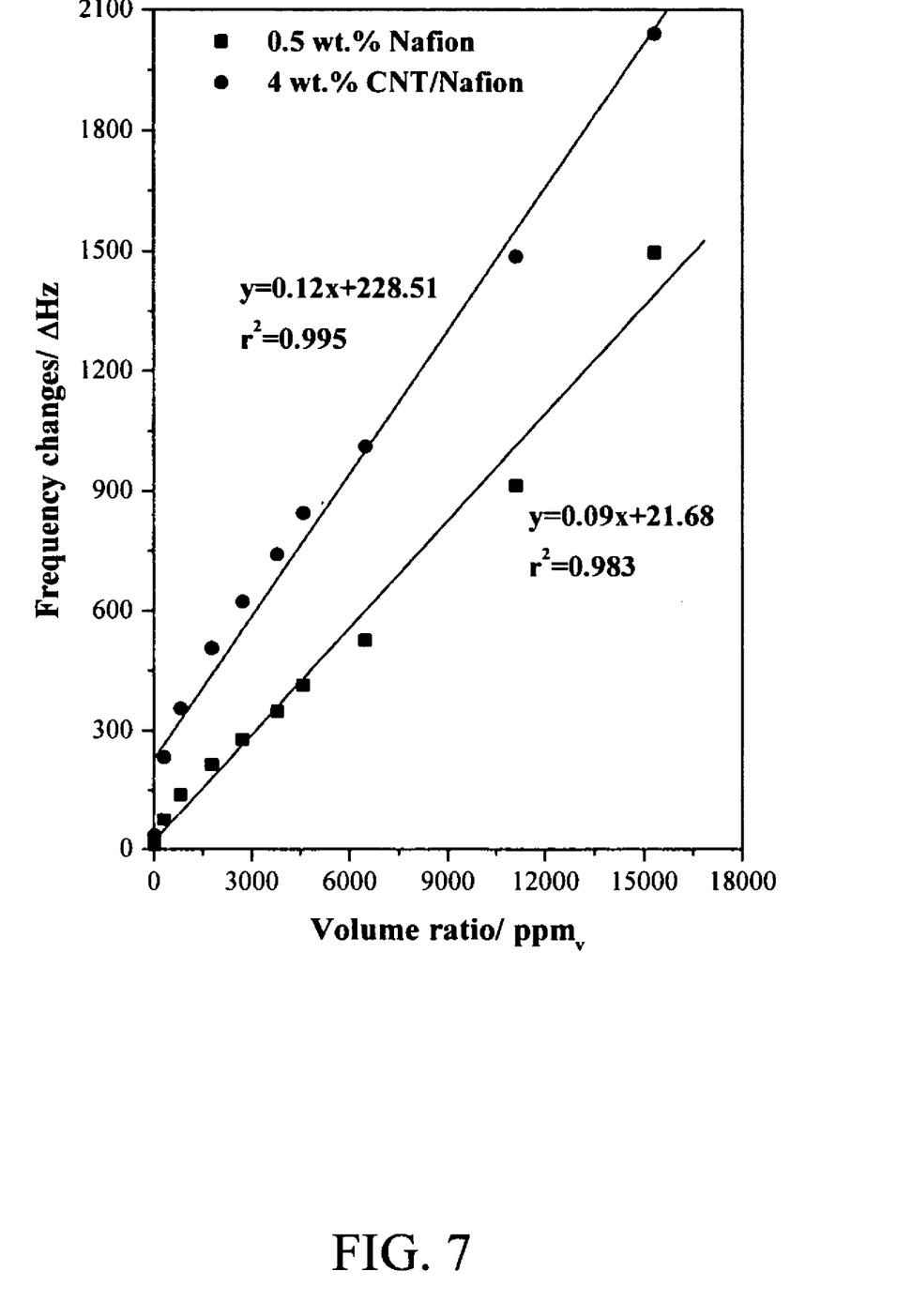
FIG. 7 shows the linear relationship between frequency changes and moisture content for humidity sensor element coated with Nafion and CNT/Nafion respectively.

FIG. 7 shows the linear relationship between frequency changes and moisture content respectively measured by Nafion humidity sensor element and CNT/Nafion humidity sensor element under trace moisture contents of 8.46-15315.73 $ppm_v$. As shown, when moisture content increased gradually from low to high, the frequency changes of both CTN/Nafion and Nafion humidity sensor element increased linearly, while the linear relationship of the former was better. The Rsqr of Nafion humidity sensor element was 0.983, while that of CNT/Nafion sensor element was 0.995 and its detection limit was 15.76 $ppm_v$.

What is claimed is:

1. A method for manufacturing humidity sensor element, comprising the steps of:
   providing a substrate;
   disposing at least a pair of electrodes on said substrate;
   mixing carbon nanotube and perfluorinated polymer solution with acid functional groups as a humidity sensing material;
   coating said humidity sensing material on said electrodes by means of spin-coating method; and
   drying said humidity sensing material to form a humidity sensor element having a single layer nanocomposite film;
   wherein the mixing ratio of carbon nanotube to perfluorinated polymer with acid functional groups is 0.01 to 20 by weight.

2. The method according to claim 1, wherein said carbon nanotube is single-walled carbon nanotube.

3. The method according to claim 1, wherein said acid functional group is sulphonic group or carboxyl group.

4. The method according to claim 1, wherein said perfluorinated polymer with acid functional group is perfluorinated sulphonic acid type ion exchange resin.

5. The method according to claim 1, wherein said electrode is selected from gold, silver, platinum or nickel cadmium alloy.

6. The method according to claim 1, wherein said substrate is any inert material that does not react with nanocomposite material, comprising silicon material, ceramic material or plastic material.

* * * * *